United States Patent [19]

Brown et al.

[11] Patent Number: 4,540,699

[45] Date of Patent: Sep. 10, 1985

[54] N-SUBSTITUTED PYRIDINONES HAVING HISTAMINE $H_2$-ANTAGONIST ACTIVITY

[75] Inventors: Thomas H. Brown, Tewin; Derek A. Rawlings, Stevenage, both of England

[73] Assignee: Smith Kline & French Laboratories Limited, Welwyn Garden City, England

[21] Appl. No.: 556,209

[22] Filed: Nov. 29, 1983

[30] Foreign Application Priority Data

Dec. 3, 1982 [GB] United Kingdom ................ 8234615

[51] Int. Cl.$^3$ .................. A61K 31/505; C07D 239/02
[52] U.S. Cl. .................................... 514/272; 544/320; 544/332; 544/333; 546/261; 546/284; 546/304; 546/339; 548/138; 548/182; 548/213; 548/351; 548/352; 548/348
[58] Field of Search ....................... 544/320; 424/251; 548/138

[56] References Cited

U.S. PATENT DOCUMENTS 3,932,644 1/1976 Durant et al. ........................ 544/320
3,980,781 9/1976 Snell et al. ........................... 544/320

OTHER PUBLICATIONS

Alfred Burger, Medicinal Chem., 2nd edition, p. 42.

Primary Examiner—Donald G. Daus
Assistant Examiner—Cecilia Shen
Attorney, Agent, or Firm—Joan S. Keps; Richard D. Foggio; Alan D. Lourie

[57] ABSTRACT

This invention relates to N-substituted pyridinone compounds which have histamine $H_2$-antagonist activity. A specific compound of this invention is 2-[2-(5-methyl-4-imidazolylmethylthio)ethylamino]-5-(1-methyl-2-oxopyridin-4-ylmethyl)pyrimidin-4-one.

27 Claims, No Drawings

N-SUBSTITUTED PYRIDINONES HAVING HISTAMINE $H_2$-ANTAGONIST ACTIVITY This invention relates to pyrimidinone derivatives, pharmaceutical compositions containing them and their use as histamine $H_2$-antagonists.

Histamine, a physiologically active compound endogenous in mammals, exerts its action by interacting with certain sites called receptors. One type of receptor is known as a histamine $H_1$-receptor (Ash and Schild, Brit. J. Pharmac. Chemother. 27 427 (1966)) and the actions of histamine mediated through these receptors are blocked by drugs commonly called "antihistamines" (histamine $H_1$-antagonists) a common example of which is mepyramine. A second type of histamine receptor is known as the $H_2$-receptor (Black et al. Nature 1972, 236, 385). These receptors are not blocked by mepyramine but are blocked by burimamide. Compounds which block these histamine Histamine $H_2$-antagonists are useful in treating $H_2$-receptors are called histamine $H_2$-antagonists. disease conditions caused by the biological effects of histamine mediated through $H_2$-receptors, for example, as inhibitors of gastric acid secretion, in the treatment of inflammation mediated through histamine $H_2$-receptors and as agents which act on the cardiovascular system, for example, as inhibitors of effects of histamine on blood pressure mediated through histamine $H_2$-receptors.

Cimetidine is an example of a histamine $H_2$-antagonist. Cimetidine has been shown to be useful in the treatment of duodenal, gastric, recurrent and stomal ulceration, and reflux oesophagitis and in the management of patients who are at high risk from haemorrhage of the upper gastrointestinal tract.

In some physiological conditions the biological actions of histamine are mediated through both histamine $H_1$- and $H_2$-receptors and blockade of both types of receptors is useful. These conditions include inflammation mediated by histamine, for example skin inflammation, and those hypersensitivity responses due to the action of histamine at $H_1$- and $H_2$-receptors, for example allergies.

Accordingly the present invention provides a compound of the formula (I):

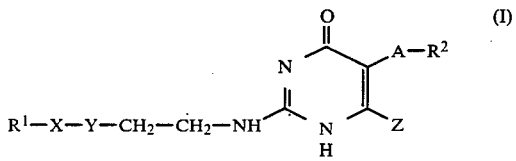

and pharmaceutically acceptable salts thereof, wherein
$R^1$ is 2- or 4- imidazolyl optionally substituted by $C_{1-6}$alkyl, halo, trifluoromethyl or hydroxymethyl; 2-thiazolyl;
2-guanidino-4-thiazolyl optionally substituted by chloro, bromo or $C_{1-6}$alkyl;
2-(5-amino-1,3,4-thiadiazolyl);
3-isothiazolyl optionally substituted by chloro or bromo;
3-(1,2,5)-thiadiazolyl optionally substituted by chloro or bromo;
2-pyridyl optionally substituted by one or more $C_{1-6}$alkyl, $C_{1-6}$alkoxy, halo, amino or hydroxy moieties or substituted in the 4-position by a group $R^3R^4N(CH_2))_m$- wherein $R^3$ and $R^4$ are independently hydrogen, $C_{1-6}$alkyl, aryl($C_{1-6}$)alkyl, heteroaryl($C_{1-6}$) alkyl, hydroxy($C_{1-6}$)alkyl, halo($C_{1-6}$)alkyl or $C_{3-8}$ cycloalkyl; or together with the nitrogen atom to which they are attached form a 5–8 membered saturated ring; and m is 1 to 6;
2-furyl or 2-thienyl either optionally substituted in the 5-position by $R^5R^6N(CH_2)_m$- wherein $R^5$ and $R^6$ are independently hydrogen, $C_{1-6}$alkyl, $C_{3-8}$cycloalkyl, halo($C_{1-6}$)alkyl, $C_{3-6}$alkenyl, aryl ($C_{1-6}$)alkyl, $C_{3-6}$alkynyl, hydroxy($C_{1-6}$)alkyl, $C_{1-3}$alkoxy($C_{1-6}$)alkyl, trifluoro($C_{1-6}$)alkyl, amino($C_{1-6}$)alkyl, $C_{1-3}$alkylamino($C_{1-6}$)alkyl or di-($C_{1-3}$)alkylamino($C_{1-6}$)alkyl; or $R^5$ and $R^6$ together with the nitrogen atom to which they are attached form a 5–8 membered saturated ring;
phenyl optionally substituted by $C_{1-6}$alkyl, $C_{1-6}$alkoxy, hydroxy, halo, trifluoromethyl, nitro, amino, $C_{1-6}$-alkylamino, $C_{1-6}$alkanoylamino, di($C_{1-6}$)alkylamino or cyano and further optionally substituted in any one of the 3—, 4—, or 5-positions by —$(CH_2)_mNR^5R^6$, —$OCH_2CH_2NR^5R^6$ or —$OCH_2CH_2CH_2NR^5R^6$;

X is methylene, or if $R^1$ is optionally substituted pyridyl or phenyl, X may also be oxygen;
Y is sulphur or methylene, provided that at least one of X and Y is methylene;
Z is hydrogen or $C_{1-6}$alkyl;
A is $C_{1-5}$methylene or -$(CH_2)_pW(CH_2)_q$ where W is oxygen or sulphur and p and q are such that their sum is from 1 to 4;
$R^2$ is a pyridone moiety substituted on the nitrogen atom by a group $R^7$ wherein $R^7$ is —$(CH_2)_rNR^8R^9$ wherein $R^8$ and $R^9$ are independently hydrogen, $C_{1-6}$alkyl, $C_{3-8}$cycloalkyl, $C_{3-6}$alkenyl, aryl($C_{1-6}$)alkyl, $C_{3-6}$alkynyl, hydroxy($C_{1-6}$)alkyl, $C_{1-3}$alkoxy($C_{1-6}$)alkyl, trifluoro($C_{1-6}$)alkyl, amino($C_{1-6}$)alkyl, $C_{1-3}$alkylamino($C_{1-6}$)alkyl or di-($C_{1-3}$)alkylamino($C_{1-6}$)alkyl; or $R^8$ and $R^9$ together with the nitrogen atom to which they are attached form a pyrrolidino, piperidino or hexahydroazepino ring, and r is 2 to 6; or $R^7$ is $C_{1-6}$alkyl, $C_{3-7}$cycloalkyl$C_{1-6}$alkyl, hydroxy-$C_{2-6}$alkyl, $C_{1-6}$alkoxy$C_{2-6}$alkyl, aryl($C_{1-6}$)alkoxy$C_{2-6}$alkyl, aryloxy$C_{2-6}$alkyl or aryl($C_{1-6}$)alkyl; and the pyridone moiety is optionally substituted by $C_{1-4}$alkyl, $C_{1-4}$alkoxy, hydroxy, halo, amino or phenoxy:
with the proviso that when X, Y and A each represent methylene, $R^7$ is $C_{1-4}$alkyl optionally substituted by hydroxy, $C_{1-4}$alkoxy or aryl, and Z is hydrogen, $R^1$ is not 2-pyridyl disubstituted, in the 3-position by halo, amino, $C_{1-4}$alkyl or $C_{3-4}$alkoxy and in the 5-position by halo, amino or $C_{1-4}$alkyl.

When used herein alkyl and alkoxy mean groups which can be straight or branched. In general preferred alkyl groups are methyl, ethyl, prop-1-yl and prop-2-yl. In general preferred alkoxy groups are methoxy, ethoxy, prop-1-oxy and prop-2-oxy. When used herein the term "aryl" includes phenyl or substituted phenyl, for example phenyl substituted by one or more $C_{1-3}$alkyl, $C_{1-3}$alkoxy or halo moieties. When used herein the term "heteroaryl" includes thienyl and furyl.

In one aspect of the compounds of this invention, $R^1$ is 2- or 4- imidazolyl optionally substituted by $C_{1-6}$alkyl, halo, trifluoromethyl or hydroxymethyl; 2-thiazolyl; 2-guanidino-4-thiazolyl optionally substituted by chloro, bromo or $C_{1-6}$alkyl; 2-(5-amino-1,3,4-thiadiazolyl); 3-isothiazolyl optionally substituted by chloro or bromo; 3-(1,2,5)-thiadiazolyl optionally substituted by chloro or bromo; 2-pyridyl optionally substituted by one or more $C_{1-6}$alkyl, $C_{1-6}$alkoxy, halo, amino or hydroxy moieties or substituted in the 4-position by a group $R^{10}R^{11}NCH_2$—wherein $R^{10}$ and $R^{11}$ are independently hydrogen or $C_{1-6}$alkyl, or together with the nitrogen atom to which they are attached form a pyrrolidino or piperidino ring; 2-furyl or 2-thienyl either optionally substituted in the 5-position by $R^{12}R^{13}N(CH_2)_m$- wherein m is 1 to 6, and $R^{12}$ and $R^{13}$ are independently hydrogen, $C_{1-6}$alkyl, $C_{3-8}$cycloalkyl, $C_{3-6}$alkenyl, aryl $(C_{1-6})$alkyl, $C_{3-6}$alkynyl, hydroxy$(C_{1-6})$alkyl, $C_{1-3}$alkoxy$(C_{1-6})$alkyl, trifluoro$(C_{1-6})$alkyl, amino$(C_{1-6})$alkyl, $C_{1-3}$alkylamino$(C_{1-6})$alkyl or di-$(C_{1-3})$alkylamino$(C_{1-6})$alkyl; or $R^{12}$ and $R^{13}$ together with the nitrogen atom to which they are attached form a pyrrolidino, piperidino or hexahydroazepino ring; phenyl optionally substituted by $C_{1-6}$alkyl, $C_{1-6}$alkoxy, hydroxy, halo, trifluoromethyl, nitro, amino, $C_{1-6}$alkylamino, $C_{1-6}$alkanoylamino, di$(C_{1-6})$alkylamino or cyano and further optionally substituted in any one of the 3-, 4-, or 5-positions by —$(CH_2)_mNR^{12}R^{13}$, —$OCH_2CH_2NR^{12}R^{13}$ or —$OCH_2CH_2CH_2NR^{12}R^{13}$;

with the proviso that if $R^1$ is optionally substituted pyridyl X is methylene.

Suitably $R^1$ is 2- or 4-imidazolyl substituted by methyl, bromo or chloro.

Suitably $R^1$ is 2-guanidino-4-thiazolyl.

Suitably $R^1$ is 2-pyridyl substituted by methyl, ethyl, hydroxy, methoxy, ethoxy, chloro, bromo or iodo. Preferably such substituents are in the 3-position, for example 3-bromo and 3-hydroxy. Suitably also $R^1$ may be 2-pyridyl substituted in the 4-position by a group $R^3R^4N(CH_2)_m$ wherein $R^3$, $R^4$ and m are as hereinbefore defined. Suitably m is one. Suitably $R^3$ and $R^4$ are independently hydrogen or $C_{1-6}$alkyl or together with the nitrogen atom to which they are attached form a pyrrolidino or piperidino ring. Preferably $R^1$ is 2-pyridyl substituted in the 4-position by dimethylaminomethyl, pyrrolidinomethyl or piperidinomethyl.

Suitably $R^1$ is 2-furanyl or 2-thienyl substituted in the 5-position by a group $R^5R^6NCH_2$—wherein $R^5$ and $R^6$ are as hereinbefore defined. Suitably $R^5$ and $R^6$ are independently selected from $C_{1-6}$alkyl, trifluoro$C_{1-6}$alkyl for example trifluoroethyl, or $R^5$ and $R^6$ together with the nitrogen atom to which they are attached form a piperidino or pyrrolidino ring.

Preferably $R^5$ is methyl or ethyl. Preferably $R^6$ is hydrogen, methyl or ethyl. In one particularly preferred aspect $R^5R^6NCH_2$— represents dimethylaminomethyl. In a further preferred aspect $R^5R^6NCH_2$— represents piperidinomethyl.

Suitably $R^1$ is phenyl either unsubstituted in the 2-position or substituted in that position by $C_{1-6}$alkyl for example methyl, $C_{1-6}$alkoxy for example methoxy, hydroxy, halo such as chloro, trifluoromethyl, amino or cyano. Preferably the phenyl ring is substituted in the 2-position by methoxy or chloro when there are no further substituents. Preferably the phenyl ring is unsubstituted in the 2-position when there is a substituent at the 3-, 4- or 5-position. Suitably such a substituent is a group $R^5R^6NCH_2$— wherein $R^5$ and $R^6$ are as hereinbefore defined. Preferably in such a group $R^5R^6NCH_2$—, $R^5$ is $C_{1-6}$alkyl for example methyl or ethyl, or is trifluoroethyl, and $R^6$ is hydrogen or $C_{1-6}$alkyl for example methyl or ethyl. In a particularly preferred aspect $R^5R^6NCH_2$— represents dimethylaminomethyl. In a further preferred aspect $R^5R^6NCH_2$— represents piperidinomethyl.

Suitably X is methylene. Preferably X is oxygen when $R^1$ is phenyl substituted by a group $R^5R^6N(CH_2)_m$—or pyridyl substituted by a group $R^5R^6N(CH_2)_m$.

Preferably Y is sulphur.

A preferred class of compounds of this invention is that wherein $R^1XYCH_2CH_2NH$— is of the sub-formula (i):

$$R^{14}R^{15}NCH_2-R^{16}-X-Y-CH_2CH_2NH- \qquad (i)$$

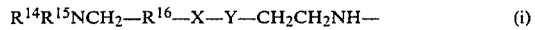

wherein $R^{14}$ and $R^{15}$ are independently $C_{1-6}$alkyl or together with the nitrogen atom to which they are attached form a pyrrolidino or piperidino ring; $R^{16}$ is 4-pyrid-2-yl, 5-furan-2-yl or 1,3-phenylene; and X and Y are as hereinbefore defined. Favourably $R^{14}$ and $R^{15}$ are both methyl or together with the nitrogen atom to which they are attached form a piperidino ring. Suitably $R^{16}$ is 5-furan-2-yl or 1,3-phenylene, preferably 5-furan-2-yl.

Preferred groups that $R^1$—X—Y— represents include: 3-methoxypyrid-2-ylethyl, 5-methyl-4-imidazolylmethylthio, and 2-guanidino-4-thiazolylmethylthio, and in particular:
3-dimethylaminomethylphenoxymethyl,
3-piperidinomethylphenoxymethyl,
5-dimethylaminomethylfuran-2-ylmethylthio,
4-dimethylaminomethylpyrid-2-ylmethylthio,
4-piperidinomethylpyrid-2-ylmethylthio,
4-dimethylaminomethylpyrid-2-yloxymethyl, and
4-piperidinomethylpyrid-2-yloxymethyl.

Preferably Z is hydrogen.

Suitably A is straight or branched alkylene, preferably straight and in particular methylene. Alternatively, A is —$(CH_2)_pW(CH_2)_q$ wherein W is oxygen, p is zero and q is one (i.e. -$OCH_2$-). Other examples of A include methoxymethyl, methylthiomethyl, methoxyethyl and methylthioethyl.

The compounds of the formula (I) are shown and described as 4-pyrimidone derivatives and these derivatives exist in equilibrium with the corresponding 6-pyrimidone tautomers. These compounds also exist to a lesser extent as the hydroxy tautomers and the pyrimidone ring may also exist in the following tautomeric forms:

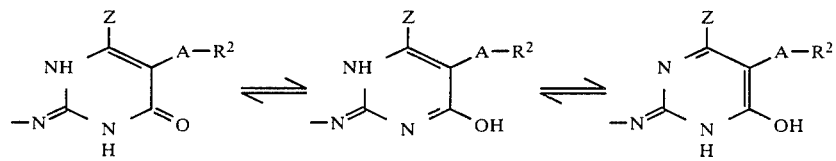

$R^2$ is a pyridone ring substituted on the nitrogen by $R^7$ and may exist in any of the isomeric forms (a)-(f):

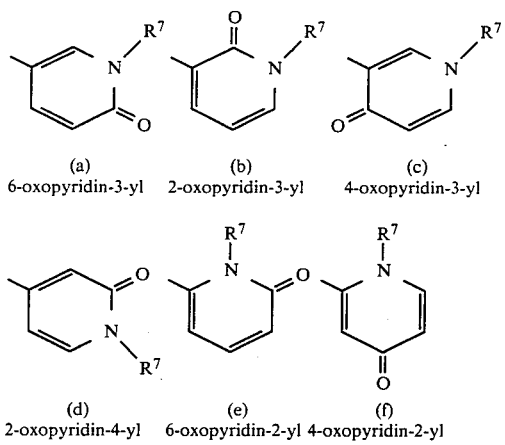

(a) 6-oxopyridin-3-yl  (b) 2-oxopyridin-3-yl  (c) 4-oxopyridin-3-yl
(d) 2-oxopyridin-4-yl  (e) 6-oxopyridin-2-yl  (f) 4-oxopyridin-2-yl Isomeric forms (a), (b), (d) and (e) are favoured, and of these forms (a) and (d) are preferred with form (d) being of particular interest.

Suitably $R^7$ is a group $R^8R^9N(CH_2)_r$— wherein r, $R^8$ and $R^9$ are as hereinbefore defined. More suitably $R^8$ is $C_{1-6}$alkyl for example methyl or ethyl, or is trifluoroethyl, and $R^9$ is hydrogen or $C_{1-6}$alkyl for example methyl or ethyl. In an another aspect $R^8R^9N$— represents piperidino or pyrrolidino.

Suitably r is 2, 3 or 4. Preferably r is 2.

Thus in one preferred aspect $R^7$ is dimethylaminoethyl, piperidinoethyl or N-(2,2,2)-trifluoroethyl-N-methyl aminoethyl.

Suitably also $R^7$ is aryl($C_{1-6}$)alkyl for example benzyl, p-hydroxybenzyl or phenethyl, or $R^7$ is $C_{1-6}$ alkyl for example methyl, ethyl, n-propyl, isopropyl, n-butyl, isobutyl or n-pentyl.

Particularly favoured values of $R^7$ are methyl, ethyl, n-butyl, benzyl or dimethylaminoethyl.

The activity of the compounds of formula (I) as histamine $H_2$-antagonists can be demonstrated by their ability to inhibit histamine-stimulated secretion of gastric acid from the lumen-perfused stomachs of rats anaesthetised with urethane, and to reverse histamine-induced inhibition of contractions of the isolated rat uterus. These are actions of histamine which, according to Ash and Schild, Brit. J. Pharmac. Chemother. 27 247 (1966), are not mediated by histamine $H_1$-receptors.

The histamine $H_2$-antagonist activity of the compounds can also be demonstrated by the inhibition of histamine-stimulated acid secretion in the Heidenhain Pouch Dog, the inhibition of histamine-induced tachycardia in the isolated guinea pig right atrium and the inhibition of histamine-induced vasodilatation in the anaesthetised cat.

The measurement of inhibition of histamine-stimulated secretion of gastric acid from the lumen-perfused stomachs of rats anaesthetised with urethane, and the measurement of inhibition of histamine-induced tachycardia in the isolated guinea pig right atrium, are detailed in European Patent Application Publication No. 0049173.

To illustrate the level of activity of the compounds of the invention we have determined that the products of the Examples have $ED_{50}$ values in the lumen-perfused rat test of less than one micromol kg$^{-1}$ i.v. and $pA_2$ values in the guinea pig atrium test of more than six.

The compound of Example 2 has an unexpected advantageous effect over analogous compounds of the art, for example Example 7 of EP-A-3677, in that it is more effective after intraduodenal administration to anaesthetised rats. The inhibition of histamine-stimulated secretion of gastric acid in rats anaesthetised with urethane was measured after administration of test compounds by intraduodenal injection and intravenous injection. For the compound of Example 2 the intraduodenal dose required to produce 50% inhibition was only 3 times the intravenous dose required to produce a similar effect, and for the compound of Example 10 the intraduodenal dose required was 10 times the intravenous dose. In contrast the compound of Example 7 of EP-A-3677 required an intraduodenal dose 500 times that of the intravenous dose required to inhibit acid secretion by 50%. Good activity after intraduodenal injection is indicative that there will good activity after oral administration.

In order to use compounds of formula (I) or pharmaceutically acceptable salts thereof for medical purposes, they are normally formulated in accordance with standard pharmaceutical practice as pharmaceutical compositions.

The invention further provides pharmaceutical compositions comprising a compound of formula (I) above or a pharmaceutically acceptable salt thereof together with a pharmaceutically acceptable carrier.

Compounds of formula (I) and their pharmaceutically acceptable salts may be administered orally, parenterally, cutaneously or rectally.

Compounds of formula (I) and their pharmaceutically acceptable salts which are active when given orally can be formulated as syrups, tablets, capsules and lozenges. A syrup formulation will generally consist of a suspension or solution of the compound or salt in a suitable liquid carrier for example, ethanol, glycerine or water with a flavouring or colouring agent. Where the composition is in the form of a tablet, any suitable pharmaceutical carrier routinely used for preparing solid formulations may be used. Examples of such carriers include magnesium stearate, starch, lactose, sucrose and cellulose.

Typical parenteral compositions consist of a solution or suspension of the compound or salt in a sterile aqueous carrier or parenterally acceptable oil.

Typical compositions for administration to the skin include lotions and creams in which the compound of formula (I) or salt thereof is contained in a liquid vehicle.

A typical suppository formulation comprises a compound of formula (I) or a pharmaceutically acceptable salt thereof which is active when administered in this way, with a binding and/or lubricating agent such as gelatin or cocoa butter or other low melting vegetable waxes or fats.

Preferably the composition is in unit dose form such as a tablet or capsule.

Each dosage unit for oral administration contains preferably from 15 to 250 mg (and for parenteral administration contains preferably from 1.5 to 25 mg) of a compound of formula (1) or a pharmaceutically acceptable salt thereof calculated as the free base.

The invention also provides a method of blocking histamine $H_2$ receptors which comprises administering to an animal an effective amount to block said receptors of a compound of formula (1) or a pharmaceutically acceptable salt thereof.

The compounds of the invention will normally be administered to a subject for the treatment of peptic ulcers and other conditions caused or exacerbated by gastric acidity in the same general manner as that employed for known histamine $H_2$-antagonists, due allowance being made in terms of dose levels for the potency of the compound of the present invention relative to known histamine $H_2$-antagonists. The daily dosage regimen for an adult patient is an oral dose of between 15 mg and 1500 mg and preferably between 20 mg and 250 mg or an intravenous, subcutaneous, or intramuscular dose of between 1.5 mg and 150 mg, and preferably between 5 mg and 20 mg of compound of formula (I) or pharmaceutically acceptable salt thereof calculated as the free base, the composition being administered 1 to 6 times per day.

The compounds of the formula (I) and pharmaceutically acceptable salts thereof may be prepared by a process which comprises:

(a) reacting a compound of the formula (II) with a compound of the formula (III):

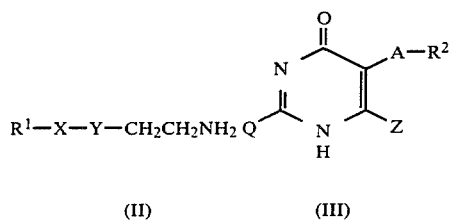

(II)            (III)

wherein $R^1$, X, A, Y, Z and $R^2$ are as hereinbefore defined and Q is a group displaceable by amine; or (b) for compounds of the formula (I) wherein X is methylene and Y is sulfur, reacting a compound of the formula (IV):

wherein $R^1$ is as hereinbefore defined and L is a moiety displaceable by thiol, with a compound of the formula (V):

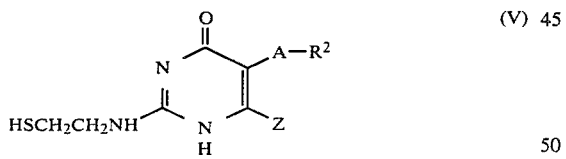

wherein A, Z and $R^2$ are as hereinbefore defined; or (c) reacting a compound of the formula (VI):

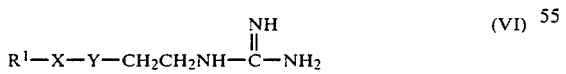

wherein $R^1$, X and Y are as hereinbefore defined, with a compound of the formula (VII):

wherein Z, A and $R^2$ are as hereinbefore defined and $R^{17}$ is $C_{1-6}$alkyl; or (d) for compounds of the formula (I) wherein $R^1$ has a $R^3R^4N(CH_2)_m$— or $R^5R^6N(CH_2)_m$— substituent, reducing a compound of the formula (VIII):

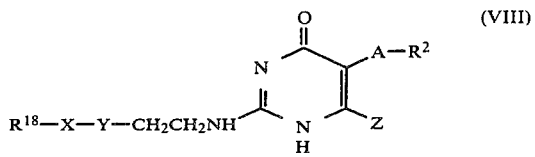

wherein $R^2$, A, Z, X and Y are as hereinbefore defined and $R^{18}$ is a group reducible to a group $R^1$ having a $R^3R^4N(CH_2)_m$— or $R^5R^6N(CH_2)_m$— substituent; or (e) reducing a compound of the formula (IX):

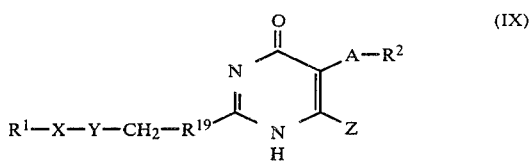

wherein $R^1$, X, Y, Z and A are as hereinbefore defined and $R^{19}$ is a group —CONH— or —C≡NH; or (f) for preparing compounds wherein $R^1$ is optionally substituted phenylene and X is oxygen, reacting a compound of the formula (X) or a chemical equivalent thereof with a compound of the formula (XI):

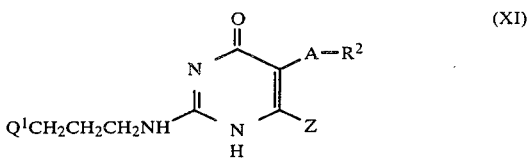

wherein $R^1$, Z, A and $R^2$ are as hereinbefore defined and $Q^1$ is a moiety displaceable by phenol or chemical equivalent thereof; or (g) for preparing compounds wherein X is methylene and Y is sulphur, reacting a compound of the formula (XII) with a compound of the formula (XIII) or chemical equivalent thereof:

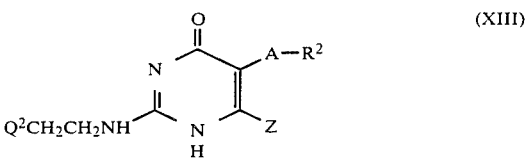

wherein $R^1$, $R^2$, A and Z are as hereinbefore defined and $Q^2$ is a group displaceable by thiol or chemical equivalent thereof;

and optionally thereafter forming a pharmaceutically acceptable salt.

In the reaction between the compounds of the formulae (II) and (III) suitably Q is nitroamino, $C_{1-6}$alkylthio, benzylthio, chloro or bromo. Of these nitroamino is preferred.

This process can be performed in the absence of solvent at an elevated temperature, or in the presence of a substantially inert polar solvent for example pyridine, anisole or $C_{1-6}$alkanol at an ambient or elevated temperature. For example when Q is nitroamino the reaction may be carried out in a $C_{1-6}$alkanol, for example ethanol or isopropanol, pyridine or anisole at the reflux temperature of the reaction mixture. When Q is methylthio the reaction may be performed in the absence of solvent at 140°–170°, or the reaction may be performed in refluxing pyridine or anisole.

In the reaction of compounds of the formulae (IV) and (V) examples of the moiety L include chloro, bromo, hydroxy, $C_{1-6}$alkoxy for example methoxy, $C_{1-6}$alkanoyloxy for example acetoxy, arylsulphonyloxy for example 4-methylbenzenesulphonyloxy or $C_{1-6}$alkylsulphonyloxy for example methanesulphonyloxy.

Preferably L is hydroxy in which case the reaction is performed under acidic conditions. When L is chloro or bromo it is preferable to perform the reaction in the presence of a strong base for example sodium ethoxide in ethanol. When L is an arylsulphonyloxy or alkylsulphonyloxy group the reaction is preferably performed under mildly basic conditions for example in pyridine solution.

The reaction between the compounds of the formulae (VI) and (VII) is suitably carried out in the presence of a base. Examples of suitable bases include alkali metal hydroxides and $C_{1-4}$alkoxides, sodium hydride, and quaternary ammonium hydroxides for example benzyltrimethylammonium hydroxide. Preferably the base is sodium ethoxide or sodium methoxide. The reaction can be carried out in the presence of a solvent the choice of which is not critical to the success of the process provided that it is substantially inert to the reagents and product. Preferably the solvent is a $C_{1-4}$alkanol, (for example, methanol, ethanol or propanol) or dimethylformamide. The reaction can be carried out at moderate temperatures, for example from room temperature to the reflux temperature of the solvent.

Preferably $R^{17}$ is methyl or ethyl.

In the compounds of the formula (VIII) in one suitable aspect $R^{18}$ has a substituent $R^3R^4N(CH_2)_s$—CO—$(CH_2)_t$— or $R^5R^6N(CH_2)_s$—CO—$(CH_2)_t$— wherein $s+t=m-1$. Favourably s and t are both zero so that the group $R^3R^4NCO$— (or $R^5R^6NCO$—) is a precursor to the group $R^3R^4NCH_2$— (or $R^5R^6NCH_2$—). The reduction of such a group $R^3R^4N(CH_2)_sCO(CH_2)_t$— may be performed with a hydride for example lithium aluminium hydride.

In an alternative aspect $R^{18}$ has a substituent CHO—$(CH_2)_{m-1}$—, which may be converted to a group $R^3R^4N(CH_2)_m$— (or $R^5R^6N(CH_2)_m$—) on reaction with an amine under conditions of reductive amination. Furthermore in another suitable aspect $R^{18}$ may have a substituent HO$(CH_2)_m$— which may be converted, for example via Cl$(CH_2)_m$—, to $R^3R^4N(CH_2)_m$— (or $R^5R^6N(CH_2)_m$—). Such transformations may be carried out in conventional manner.

In particular compounds of the formula (I) wherein $R^1$ is furyl or thienyl either substituted by a $R^5R^6NCH_2$— group may be prepared from the corresponding compounds of formula (I) wherein $R^1$ is substituted by hydrogen at the relevant position, by reaction with a Mannich reagent, for example formaldehyde and an amine $R^5R^6NH$ or salt thereof. This reaction may be carried out by treatment of an amine salt with aqueous formaldehyde and a compound of the formula (I) (wherein $R^1$ is substituted by hydrogen at the relevant position), or by refluxing an amine salt with paraformaldehyde and a compound of the formula (I) (wherein $R^1$ is substituted by hydrogen at the relevant position) in a convenient solvent such as ethanol. Alternatively where $R^5$ and $R^6$ are both $C_{1-4}$alkyl, the Mannich reagent may be a di-($C_{1-4}$alkyl)methylene ammonium salt for example dimethylmethylene ammonium chloride or iodide, or may be a bis di-$C_{1-4}$alkylaminomethane, for example bis(dimethylamino)methane.

Any group in the remainder of the molecule that is capable of reacting with a Mannich reagent may be optionally protected during the reaction, and may be subsequently deprotected in conventional manner.

The compounds of the formula (IX) may be reduced to form compounds of the formula (I) for example using hydrides.

In the reaction between the compounds of the formulae (X) and (XI) suitably $Q^1$ is chloro or bromo. Suitably the reaction is performed under basic conditions, for example the anion of the compound of the formula (X) may be generated, for example using sodium hydride. The reaction is performed in a suitable aprotic solvent for example dimethylformamide at a non-extreme temperature for example between 0° C. and 100° C., suitably between ambient and 70° C.

Suitably in the reaction between the compounds of the formulae (XII) and (XIII) $Q^2$ is chloro, bromo, arylsulphonyloxy for example 4-methylbenzenesulphonyloxy or $C_{1-6}$alkylsulphonyloxy for example methanesulphonyloxy. Such reactions are generally performed in the presence of a base for example triethylamine, an alkoxide or a hydroxide.

Pharmaceutically acceptable acid addition salts of the compounds of the formula (I) may be prepared from the corresponding base of the compounds of the formula (I) in conventional manner. For example the base may be reacted with an acid in a $C_{1-4}$alkanol, or an ion-exchange resin may be used. The salts of the compounds of the formula (I) may be interconverted using ion-exchange resins. Non-pharmaceutically acceptable salts are therefore of use as they can be converted to pharmaceutically acceptable salts.

Suitable pharmaceutically acceptable acid addition salts of the compounds of the formula (I) include those formed with hydrochloride, hydrobromic, sulphuric, phosphoric, acetic, citric, maleic, lactic, ascorbic, fumaric, oxalic, methanesulphonic and ethanesulphonic acids.

The compounds of the formulae (II), (IV) and (XII) are preparable by the methods described in EPA-3677, 4793, 13071, 15138, 17679, 17680 and 49173 and GB-A-2030979.

The compounds of the formula (III) wherein Q is nitroamino may be prepared by the reaction of a compound of the formula (VII) with nitroguanidine.

The compounds of the formula (III) wherein Q is $C_{1-6}$alkylthio or benzylthio may be prepared by the reaction of a compound of the formula (VII) with thiourea followed by alkylation or benzylation.

The compounds of the formula (VIII) may be prepared in a manner analogous to that described for the preparation of compounds of the formula (I), for example reacting a compound of the formula (III) with an analogue of a compound of the formula (II) wherein $R^1$ is replaced by provided that is suitably protected as necessary.

The compounds of the formula (IX) wherein $R^{19}$ is $CH=N$ may be prepared by the reaction of a compound of the formula (XIV) with a compound of the formula (XV):

$$R^1XYCH_2CHO \qquad (XIV)$$

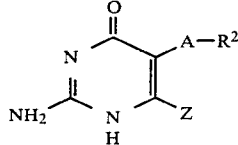
(XV)

wherein $R^1$, $R^2$, A, Z, Y and X are as hereinbefore defined, optionally in the presence of an acid catalyst. The compounds of the formula (IX) wherein $R^{19}$ is —CONH— may be prepared by the reaction of a compound of the formula (XV) with an activated derivative of a compound of the formula (XVI):

$$R^1XYCH_2CO_2H \qquad (XVI)$$

wherein $R^1$, X and Y are as hereinbefore defined. Suitable active derivatives are acyl halides, anhydrides and activated esters. The aldehydes of the formula (XIV) may be prepared for example by reacting a compound of the formula (XVII):

$$R^1\text{—OH} \qquad (XVII)$$

wherein $R^1$ is as hereinbefore defined, with a protected bromopropionaldehyde (for example protected as a cyclic acetal) and deprotecting. The acid of the formula (XVI) and derivatives thereof may be prepared in similar manner for example by reacting a compound of the formula (XVII) with a protected bromopropionic acid and if necessary deprotecting and/or converting to the desired activated acid derivative.

The compounds of the formulae (V), (XI) and (XIII) may be prepared for example by methods analogous to that described for the reaction of compounds of the formulae (II) and (III), that is reacting a compound of the formula (III) with $HSCH_2CH_2NH_2$, $Q^1CH_2CH_2CH_2NH_2$, or $Q^2CH_2CH_2NH_2$, wherein the nature of the groups $Q^1$ and $Q^2$ is such that the desired reaction occurs.

The compounds of the formula (VII) wherein Z is hydrogen may be prepared for example by the reaction of a compound of the formula (XVIII):

$$R^{17}OC\text{—}CH_2\text{—}A\text{—}R^2 \qquad (XVIII)$$
$$\parallel$$
$$O$$

wherein A, $R^2$ and $R^{17}$ are as hereinbefore defined, with a formylating agent, for example a $C_{1-6}$alkyl formate such as ethyl formate, in the presence of a strong base. Suitably sodium hydride in 1,2-dimethoxyethane or tetrahydrofuran may be used. In an alternative sodium in ether may be used.

The compounds of the formula (VII) wherein Z is hydrogen or $C_{1-6}$alkyl may be prepared in conventional manner, such as adaptation of the disclosure of British Specification 1582527.

The compounds of the formula (VI) may be prepared by the reaction of a compound of the formula (II) with a compound of the formula (XIX):

$$\begin{array}{c} NH \\ \parallel \\ T\text{—}C\text{—}NH_2 \end{array} \qquad (XIX)$$

wherein T is a leaving group such as methylthio.

During the processes described in this specificaion any groups may be optionally protected, if appropriate, in conventional manner. For example suitable amino-protecting groups for the processes described herein include tertiarybutyloxycarbonyl removable by trifluoroacetic acid, benzyloxycarbonyl removable by hydrogenolysis or hydrobromic acid, and phthaloyl removable by hydrazine. Suitable hydroxy protecting groups include benzyloxycarbonyl, methoxymethyl, methylthiomethyl, tetrahydropyranyl, benzyl, $C_{1-6}$alkyl for example methyl, and acyl for example formyl or acetyl.

The following Examples serve to illustrate this invention.

EXAMPLES

EXAMPLE 1

2-[2-(5-Methyl-4-imidazolylmethylthio)ethylamino]-5-(1-methyl-2-oxopyridin-4-ylmethyl)pyrimidin-4-one (i) Ethyl β-(N-methyl-2-oxo-4-pyridyl)acrylate N-Methyl-4-formyl-2-pyridone* (30.17 g), monoethyl malonate (38.15 g), pyridine (150 ml) and piperidine (3 ml) were stirred under reflux for 6½ hours. The reaction mixture was evaporated under reduced pressure to afford a residue which was crystallised from aqueous isopropanol to give ethyl β-(N-methyl-2-oxo-4-pyridyl)acrylate as a pale yellow solid (18.44 g), m.p. 126°–7° C.

*Prepared by the method disclosed in Chemical Abstracts 54, 14244a (1960).

(ii) Ethyl β-(N-methyl-2-oxo-4-pyridyl)propionate

Ethyl β-(N-methyl-2-oxo-4-pyridyl)acrylate (26.28 g) in ethanol (170 ml) was hydrogenated over 5% palladium on charcoal (0.25 g) at 350 KPa (50 psi), with gentle warming, until theoretical uptake had been exceeded. The reaction mixture was filtered through diatomaceous earth and evaporated under reduced pressure to give ethyl β-(N-methyl-2-oxo-4-pyridyl)propionate as an oil (27.03 g) which was sufficiently pure for the next stage of the reaction sequence.

(iii) Ethyl α-formyl-β-(N-methyl-2-oxo-4-pyridyl)propionate

To a stirred suspension of 57% sodium hydride in oil (6.55 g) in dimethoxyethane (40 ml) at −5° C., was added dropwise over 40 minutes a mixture of ethyl β-(N-methyl-2-oxo-4-pyridyl)propionate (26.05 g) and ethyl formate (13.83 g) whilst maintaining the reaction temperature at −5° C. The temperature of the reaction mixture was slowly allowed to rise to ambient at which temperature it was stood for three days. The reaction mixture was poured on to ice, extracted with diethyl ether (3×100 ml) and the combined organic layers were washed with water (2×20 ml). The aqueous layer and washings were acidified to pH 4 with 2 N sulphuric acid whereupon a solid came out of solution. The mixture was kept at 0° C. for two hours, and the solid filtered off and dried in vacuo to afford ethyl α-formyl-β-(N-methyl-2-oxo-4-pyridyl)propionate (15.27 g) as a solid; recrystallisation from isopropanol afforded a solid, m.p. 164-5-165.5° C.

(iv) 2-Nitroamino-5-(1-methyl-2-oxopyridin-4-ylmethyl)-pyrimidin-4-one

A solution of sodium (2.31 g) in methanol (50 ml) was prepared. To this was added, with stirring, nitroguanidine (9.28 g) (containing 25% w/w water) and methanol 910 ml). The mixture was stirred under reflux for one hour and a semi-solution, semi-suspension of ethyl α-formyl-β-(N-methyl-2-oxo-4-pyridyl)propionate (15.87 g) in methanol (60 ml) was added over the period of one hour. The reaction mixture was refluxed for 20 hours, and evaporated under reduced pressure to afford an oil. This oil was dissolved in water (120 ml), extracted with chloroform (3×40 ml), and the combined organic layers were washed with water (3×20 ml). The combined aqueous layer and aqueous washings were taken to pH 4 with glacial acetic acid. A crystalline solid slowly precipitated, with cooling, to afford on washing and drying in vacuo 2-nitroamino-5-(1-methyl-2-oxopyridin-4-ylmethyl)pyrimidin-4-one (9.34 g) as a solid, m.p. 245°-248° C. (decomp).

(v) 2-[2-(5-Methyl-4-imidazolylmethylthio)-ethylamino]-5-(1-methyl-2-oxopyridin-4-ylmethyl)pyrimidin-4-one 2-(5-Methyl-4-imidazolylmethylthio)ethylamine (1.37 g) and 2-nitroamino-5-(1-methyl-2-oxopyridin-4-ylmethyl)pyrimidin-4-one (2.08 g) were refluxed in ethanol (10 ml) for 24 hours. The reaction mixture was cooled and evaporated under reduced pressure to afford a glassy residue which was washed with hot water yielding a white solid. This solid was filtered off, washed with water and recrystallised from methanol to yield 2-[2-(5-methyl-4-imidazolylmethylthio)ethylamino]-5-(1-methyl-2-oxopyridin-4-ylmethyl)pyrimidin-4-one (1.61 g); recrystallisation from aqueous methanol afforded the title compound, m.p. 202.5°-203.5° C.

EXAMPLE 2

2-[2-(2-Dimethylaminomethyl-5-furylmethylthio)ethylamino]-5-(1-methyl-2-oxopyridin-4-ylmethyl)-pyrimidin-4-one 2-Nitroamino-5-(1-methyl-2-oxopyridin-4-ylmethyl)-pyrimidin-4-one (2.08 g) and 2-(2-dimethylaminomethyl-5-furylmethylthio)ethylamine (1.82 g) were refluxed in ethanol (10 ml) for 22 hours. The reaction mixture was evaporated under reduced pressure to afford an oil which on trituration with diethyl ether gave a solid. This solid was collected by filtration, washed with diethyl ether and recrystallised from isopropanol to yield 2-[2-(2-dimethylaminomethyl-5-furylmethylthio)ethylamino]-5-(1-methyl- 2-oxopyridin-4-ylmethyl)-pyrimidin-4-one (1.41 g); recrystallisation from isopropanol afforded material with m.p. 129°-132° C.

A portion of the title compound was treated with dilute ethanolic HCl. The reaction mixture was evaporated under reduced pressure and crystallised from methanol-2N hydrochloric acid to yield 2-[2-(2-dimethylaminomethyl-5-furylmethylthio)ethylamino]-5-(1-methyl-2-oxopyridin-4-ylmethyl)pyrimidin-4-one trihydrochloride, m.p. 185°-188° C.

EXAMPLE 3

2-[2-(5-Methyl-4-imidazolylmethylthio)-ethylamino]-5-(1-n-butyl-2-oxopyridin-4-ylmethyl)pyrimidin-4-one (i) N-n-Butyl-4-(ethylenedioxymethyl)-2-pyridone 4-(Ethylenedioxymethyl)pyridine (105.82 g) and n-butyl bromide (97.61 g, 76.5 ml) were stirred at 95°-100° C. for 1½ hours. The reaction mixture was cooled, dissolved in water (200 ml) and washed with diethyl ether (2×50 ml) to remove any unreacted n-butyl bromide. The combined ether extracts were washed with water (2×25 ml). The aqueous layer and aqueous washings were added to a solution of potassium ferricyanide (465 g) in water (1600 ml), the solution was stirred for 30 minutes and cooled to 10° C. Potassium hydroxide (160 g) was added with stirring over 60 minutes whilst maintaining the temperature of the reaction at 10°-15° C. The reaction mixture was stirred for a further 45 minutes and allowed to stand overnight whereupon some solid separated out. Benzene (300 ml) was added and the mixture stirred for 90 minutes. The solid was removed by filtration and the benzene layer of the filtrate was collected. The solid was washed and the aqueous layer was extracted with benzene (2×300 ml). The benzene extracts were combined, washed with water (2×50 ml), dried over MgSO$_4$ and evaporated under reduced pressure to afford N-n-butyl-4-(ethylenedioxymethyl)-2-pyridone (94.49 g) as an oil.

(ii) N-n-Butyl-4-formyl-2-pyridone

N-n-Butyl-4-(ethylenedioxymethyl)-2-pyridone (94.49 g) and 3% hydrochloric acid (50 ml of concentrated hydrochloric acid made up to 570 ml) were heated on a steam bath for 30 minutes. The solution was allowed to cool overnight and taken to pH 8 with potassium carbonate solution. The reaction mixture was extracted into chloroform (6×200 ml), and the combined chloroform extracts were washed with water (2×50 ml), dried over MgSO$_4$ and evaporated under reduced pressure to afford an oil. This oil was washed with petroleum ether (40°-60°) and on cooling N-n-butyl-4-formyl-2-pyridone was obtained as a solid (64.37 g), m.p. 36°-40° C.

(iii) β-(N-n-Butyl-2-oxo-4-pyridyl)acrylic acid

N-n-Butyl-4-formyl-2-pyridone (68.71 g), malonic acid (39.90 g), pyridine (225 ml) and piperidine (4.5 ml) were stirred under reflux for 6 hours. The reaction mixture was evaporated under reduced pressure to afford an oil, to which was added water and a small amount of ammonia ('880 solution) to aid dissolution. The solution was taken to pH 4 with acetic acid, the solvent volume was diminished under reduced pressure and acetone added to precipitate a solid. After cooling at 0° C. for a few hours the solid was collected by filtration, washed with acetone and dried in vacuo to afford β-(N-n-butyl-2-oxo-4-pyridyl)acrylic acid (62.06 g) as a white solid, m.p. 131°-134° C.

(iv) Ethyl β-(N-n-butyl-2-oxo-4-pyridyl)acrylate

β-(N-n-Butyl-2-oxo-4-pyridyl)acrylic acid (62.03 g) and concentrated sulphuric acid (15 ml) were refluxed in ethanol (250 ml) for 21 hours. As a little undissolved solid was present in the reaction mixture more concentrated sulphuric acid (10 ml) in ethanol (100 ml) was added and the mixture refluxed for a further 5 hours. The solution was partially evaporated under reduced pressure and poured on to a mixture of '880 ammonia and ice. The ice was allowed to melt whereupon the oil that had separated out was extracted into diethyl ether (3×120 ml), dried over MgSO$_4$ and evaporated under reduced pressure to give an oil which on standing at 0° C. afforded ethyl B-(N-n-butyl-2-oxo-4-pyridyl)acrylate (59.50 g) as a crystalline solid, m.p. 55.5°–57.5° C.

(v) Ethyl β-(N-n-butyl-2-oxo-4-pyridyl)propionate

Ethyl β-(N-n-butyl-2-oxo-4-pyridyl)acrylate (59.50 g) in ethanol (150 ml) was hydrogenated over 5% palladium on charcoal (0.45 g) at 315 KPa (45 psi), with gentle warming. When the theoretical uptake of hydrogen had been exceeded the reaction mixture was filtered and the filtrate evaporated under reduced pressure to afford an oil. This oil was washed with petroleum ether (40°–60°) to yield ethyl β-(N-n-butyl-2-oxo-4-pyridyl)propionate (58.19 g).

(vi) Ethyl α-formyl-β-(N-n-butyl-2-oxo-4-pyridyl)propionate

To a stirred suspension of 50% sodium hydride in oil (13.89 g) in dimethoxyethane (100 ml) at −2° C., was added dropwise over 90 minutes, a mixture of ethyl β-(N-n-butyl-2-oxo-4-pyridyl)propionate (58.19 g) and ethyl formate (25.73 g), the reaction temperature being maintained below 5° C. The reaction mixture was then allowed to warm to room temperature overnight, poured on to ice and extracted successively into petroleum ether (40°–60°) (150 ml) and diethyl ether (3×100 ml). The combined organic extracts were washed with water (40 ml); and the aqueous layer and aqueous washings were taken to pH 5 with glacial acetic acid. A brown oil came out of solution which was extracted into ethyl acetate (3×150 ml). The combined ethyl acetate extracts were washed with water (2×30 ml), dried over MgSO$_4$ and evaporated under reduced pressure. The residue was washed with petroleum ether (40°–60°) and dried in vacuo to afford as a pale brown solid, ethyl α-formyl-β-(N-n-butyl-2-oxo-4-pyridyl)propionate (54.84 g).

(vii) 2-Nitroamino-5-(1-n-butyl-2-oxopyridin-4-ylmethyl)-pyrimidin-4-one

To a stirred solution of sodium (6.77 g) in methanol (120 ml) was added nitroguanidine (27.25 g. containing 25% water) and methanol (30 ml). The mixture was refluxed for 45 minutes and then was added dropwise ethyl α-formyl-β-(N-n-butyl-2-oxo-4-pyridyl)propionate (54.85 g) in methanol (150 ml) over 90 minutes. The reaction mixture was refluxed for 23 hours and evaporated under reduced pressure to give an oil. This oil was dissolved in water (200 ml) and extracted with chloroform (3×65 ml). The combined chloroform extracts were washed with water (2×35 ml). The combined aqueous layer and aqueous washings were taken to pH 5 with glacial acetic acid whereupon a brown oil came out of solution. This was dissolved with warming in isopropanol (75 ml) and cooled at 0° C. overnight to yield after filtration, washing and drying in vacuo 2-nitroamino-5-(1-n-butyl-2-oxopyridin-4-ylmethyl)-pyrimidin-4-one as a solid (19.46 g), recrystallisation from aqueous acetic acid gave material with m.p. 198°–201° C.

(viii) 2-[2-(5-Methyl-4-imidazolylmethylthio)ethylamino]-5-(1-n-butyl-2-oxopyridin-4-ylmethyl)pyrimidin-4-one 2-(5-Methyl-4-imidazolylmethylthio)ethylamine (1.37 g) and 2-nitroamino-5-(1-n-butyl-2-oxopyridin-4-ylmethyl)pyrimidin-4-one (2.39 g) were refluxed in pyridine (12 ml) for 17 hours. The reaction mixture was evaporated under reduced pressure and the residue washed with hot water. The mixture was allowed to cool and the water was decanted to give the title compound as a residue. Ethanolic HCl was added with warming and on subsequent cooling the trihydrochloride salt of 2-[2-(5-methyl-4-imidazolylmethylthio)ethylamino]-5-(1-n-butyl-2-oxopyridin-4-ylmethyl)pyrimidin-4-one was obtained as a solid (2.50 g); recrystallisation from ethanolic HCl afforded material, m.p. 170°–173.5° C.

EXAMPLE 4

2-[2-(2-Dimethylaminomethyl-5-furylmethylthio)ethylamino]-5-(1-n-butyl-2-oxopyridin-4-ylmethyl)-pyrimidin-4-one 2-(2-Dimethylaminomethyl-5-furylmethylthio)ethylamine (1.44 g) and 2-nitroamino-5-(1-n-butyl-2-oxopyridin-4-ylmethyl)pyrimidin-4-one (1.76 g) were refluxed in pyridine (10 ml) for 24 hours. The reaction mixture was evaporated under reduced pressure to afford an oil which was washed with hot water. The mixture was allowed to cool overnight and the water was decanted to give the title compound as a residue. Ethanolic HCl (3 ml) and isopropanol were added with warming to give a solution which was evaporated under reduced pressure to give a residue which was recrystallised from isopropanolethanolic HCl to give 2-[2-(2-dimethylaminomethyl-5-furylmethylthio)ethylamino]-5-(1-n-butyl-2-oxopyridin-4-ylmethyl)-pyrimidin-4-one as a trihydrochloride salt (2.67 g), m.p. 169°–171.5° C.

EXAMPLE 5

2-[2-(2-Guanidino-4-thiazolylmethylthio)ethylamino]-5-(1-n-butyl-2-oxopyridin-4-ylmethyl)pyrimidin-4-one To a solution of sodium (0.46 g) in ethanol (12 ml) was added 2-guanidino-4-[2-(2-aminoethyl)thiomethyl]-thiazole dihydrochloride (3.04 g) and the solution was stirred for 2½ hours before filtration through Hyflo. The filtrate was evaporated under reduced pressue to afford a residue which was refluxed for 20 hours with 2-nitroamino-5-(1-n-butyl-2-oxopyridin-4-ylmethyl)-pyrimidin-4-one (2.55 g) in pyridine (12 ml). The reaction mixture was evaporated under reduced pressure and the residue washed with hot water. The mixture was allowed to cool overnight and the water was decanted to give the title compound as a residue. This residue was dissolved in ethanolic HCl and methanol, treated with charcoal, filtered, evaporated under reduced pressure and recrystallised from ethanolmethanol to yield 2-[2-(2-guanidino-4-thiazolylmethylthio)ethylamino]-5-(1-n-butyl-2-oxopyridin-4-ylmethyl)-pyrimidin-4-one as a trihydrochloride salt (2.27 g), m.p. 158°–162° C.

EXAMPLE 6

2-[2-(5-Methyl-4-imidazolylmethylthio)ethylamino]-5-(1-benzyl-2-oxopyridin-4-ylmethyl)pyrimidin-4-one

(i) Ethyl β-(2-hydroxy-4-pyridyl)propionate

Ethyl β-(2-methoxy-4-pyridyl)propionate (89.1 g) and ethanolic HCl (200 ml) were stirred under reflux in ethanol (900 ml) for 48 hours. The reaction mixture was evaporated under reduced pressure to give an oily residue which was dissolved in water (300 ml). This solution was taken to pH9 with potassium carbonate solution and extracted into ethyl acetate (6×250 ml). The combined ethyl acetate extracts were washed with water, dried over MgSO$_4$ and evaporated under reduced pressure to afford an oil which solidified to give white crystals of ethyl β-(2-hydroxy-4-pyridyl)propionate which were washed with petroleum ether (40°–60°) and dried in vacuo (59.58 g), m.p. 73°–76.5° C.

(ii) Ethyl β-(N-benzyl-2-oxo-4-pyridyl)propionate

To a cooled solution of sodium (3.25 g) in ethanol (75 ml) was added a solution of ethyl β-(2-hydroxy-4-pyridyl)propionate (25.38 g) in ethanol (150 ml). This mixture was stirred for 45 minutes and then benzyl chloride (16.58 g) in ethanol (125 ml) was added. The reaction mixture was stirred under reflux for 9 hours, allowed to cool and evaporated under reduced pressure. The residue was taken up in water (150 ml) and diethyl ether (150 ml), the aqueous layer was separated and washed with diethyl ether (2×120 ml). The combined ether extracts were washed with water, dried over MgSO$_4$ and evaporated under reduced pressure to yield ethyl β-(N-benzyl-2-oxo-4-pyridyl)propionate (30.29 g) as an oil.

(iii) Ethyl α-formyl-β-(N-benzyl-2-oxo-4-pyridyl)propionate

To a cooled (0° C.), stirred suspension of 50% sodium hydride in oil (6.37 g) in dimethoxyethane (80 ml) was added dropwise over 25 minutes a mixture of ethyl β-(N-benzyl-2-oxo-4-pyridyl)propionate (30.29 g) and ethylformate (11.80 g), whilst maintaining the reaction temperature between 5°–8° C. The reaction mixture was allowed to warm slowly to room temperature overnight and then was poured on to ice. A brown solution formed which was extracted successively with petroleum ether (40°–60° C.) (60 ml) and diethyl ether (70 ml). The combined organic extracts were washed with water. The combined aqueous layer and aqueous washings were taken to pH 5 with glacial acetic acid. The solution was cooled whereupon a solid appeared which was collected by filtration, washed with water, washed with ethyl acetate and dried in vacuo to yield ethyl α-formyl-β-(N-benzyl-2-oxo-4-pyridyl)propionate (22.52 g), m.p. 140°–143° C.

(iv) 2-Nitroamino-5-(1-benzyl-2-oxopyridin-4-ylmethyl)pyrimidin-4-one

To a stirred solution of sodium (2.76 g) in methanol (50 ml) was added nitroguanidine (11.10 g. containing 25% water) and methanol (10 ml). The mixture was refluxed for 45 minutes and then ethyl α-formyl-β-(N-benzyl-2-oxo-4-pyridyl)propionate (25.07 g) in methanol (90 ml) was added over one hour. The reaction mixture was refluxed for 24 hours, cooled and evaporated under reduced pressure to afford an oily residue which was dissolved in water (100 ml). The solution was extracted with chloroform (3×50 ml) and the combined chloroform extracts were washed with water (3×25 ml). The combined aqueous layer and aqueous washings were taken to pH 5 with glacial acetic acid to give an oily solid. Isopropanol (35 ml) was added with warming to cause dissolution, on cooling a solid formed which was collected by filtration, washed with water, washed with isopropanol and recrystallised from water-acetic acid to give white crystals of 2-nitroamino-5-(1-benzyl-2-oxopyridin-4-ylmethyl)pyrimidin-4-one (10.40 g), m.p. 200°–201° C.

(v) 2-[2-(5-Methyl-4-imidazolylmethylthio)ethylamino]-5-(1-benzyl-2-oxopyridin-4-ylmethyl)pyrimidin-4-one 2-[2-(5-Methyl-4-imidazolylmethylthio)ethylamine (1.28 g) and 2-nitroamino-5-(1-benzyl-2-oxopyridin-4-ylmethyl)pyrimidin-4-one (2.47 g) were refluxed in pyridine (12 ml) for 20 hours. The reaction mixture was evaporated under reduced pressure and the glassy residue washed with hot water. The mixture was allowed to cool and the water was decanted to give the title compound as a residue. This residue was taken up in isopropanol, treated with ethanolic HCl, evaporated under reduced pressure and crystallised from ethanol-methanol to give 2-[2-(5-methyl-4-imidazolylmethylthio)ethylamino]-5-(1-benzyl-2-oxopyridin 4-ylmethyl)-pyrimidin-4-one as a trihydrochloride salt (3.23 g): recrystallisation gave material with m.p. 185.5°–189° C.

EXAMPLE 7

2-[2-(2-Dimethylaminomethyl-5-furylmethylthio)ethylamino]-5-(1-benzyl-2-oxopyridin-4-ylmethyl)pyrimidin-4-one 2-(2-Dimethylaminomethyl-5-furylmethylthio)ethylamine (2.28 g) and 2-nitroamino-5-(1-benzyl-2-oxopyridin-4-ylmethyl)pyrimidin-4-one (2.80 g) were refluxed in pyridine (12 ml) for 20 hours. The reaction mixture was evaporated under reduced pressure and the resultant oily residue was washed with hot water. The mixture was allowed to cool and the water was washed twice with cold water and recrystallised from isopropanol to yield 2-[2-(2-dimethylaminomethyl-5-furylmethylthio)ethylamino]-5-(1-benzyl-2-oxopyridin-4-ylmethyl)pyrimidin-4-one (3.33 g), m.p. 95.5°–98° C.

EXAMPLE 8

2-[2-(2-Dimethylaminomethyl-5-furylmethylthio)ethylamino]-5-[1-(2-dimethylaminoethyl)-2-oxopyridin-4-ylmethyl)pyrimidin-4-one

(i) Ethyl β-[N-(2-dimethylaminoethyl)-2-oxo-4-pyridyl]propionate

To a cooled solution of sodium (7.50 g) in ethanol (150 ml) was added a solution of ethyl β-(2-hydroxy-4-pyridyl)propionate (29.07 g) in ethanol (175 ml). After the solution was stirred for 40 minutes a solution of dimethylaminoethyl chloride hydrochloride (21.78 g) in ethanol (175 ml) was added and the reaction mixture was stirred under reflux for 6 hours and then was allowed to cool overnight. The reaction mixture was filtered and evaporated under reduced pressure to remove most of the solvent. Water (150 ml) was added and the solution was extracted with ethyl acetate (3×200 ml). The combined ethyl acetate extracts were dried over MgSO$_4$ and evaporated under reduced pressure to yield an oil which was subjected to medium pressure column chromatography (using Kieselgel 60 silica gel 70–230 mesh-pre column and 230–400 mesh-main column) with gradient elution (dichloromethane→10% methanolic dichloromethane). The fractions containing the desired product were combined and evaporated under reduced pressure to yield ethyl β-[N-(2-dimethylaminoethyl)-2-oxo-4-pyridyl]propionate (25.43 g) as an oil.

(ii) Ethyl α-formyl-β-[N-(2-dimethylaminoethyl)-2-oxo-4-pyridyl]propionate

To a stirred, cooled suspension of 50% sodium hydride in oil (5.73 g) in dimethoxyethane (50 ml) was added dropwise over 50 minutes a mixture of ethyl β-[N-(2-dimethylaminoethyl)- 2-oxo-4-pyridyl]propionate (25.43 g) and ethyl formate (10.60 g). The reaction temperature was maintained below 3° C., and then was allowed to warm to room temperature overnight. The reaction mixture was poured on to ice and the resultant brown solution was extracted with petroleum ether (40°–60°) (80 ml) and diethyl ether (3×60 ml). The combined organic extracts were washed with water (20 ml). The combined aqueous solution and aqueous washings were taken to pH 5 with glacial acetic acid, the solvent volume was halved by evaporation under reduced pressure and taken to pH 8 with sodium bicarbonate solution. The solvents were removed by thorough evaporation under reduced pressure and the residue taken up in hot isopropanol-acetone, filtered over diatomaceous earth and evaporated under reduced pressure to yield an oil which was washed with petroleum ether (40°–60°) to afford as a brown oil, ethyl α-formyl-β-(N-(2-dimethylaminoethyl)-2-oxo-4-pyridyl]propionate (25.05 g).

(iii) 2-Nitroamino-5-[1-(2-dimethylaminoethyl)-2-oxopyridin-4-ylmethyl]pyrimidin-4-one To a stirred solution of sodium (2.94 g) in methanol (65 ml) was added nitroguanidine (11.81 g, containing 25% w/w water) and methanol (20 ml). The mixture was stirred at reflux for 60 minutes, and then a solution of ethyl α-formyl-β-(N-(2-dimethylaminoethyl)-2-oxo-4-pyridyl]propionate (25.05 g) in methanol (75 ml) was added dropwise over 90 minutes. The reaction mixture was stirred under reflux for a further 21 hours. The reaction mixture was evaporated under reduced pressure, dissolved in water (150 ml) and extracted with chloroform (3×35 ml). The combined chloroform extracts were washed with water (2×10 ml). The combined aqueous layer and aqueous washings were taken to pH 4 with glacial acetic acid. The solvent was then evaporated under reduced pressure and a solid by-product crystallised from ethanol. The mother liquors were evaporated and another crystallisation from ethanol gave a further solid by-product. The mother liquor was evaporated under reduced pressure to afford 2-nitroamino-5-[1-(2-dimethylaminoethyl)-2-oxopyridin-4-ylmethyl]pyrimidin-4-one (11.26 g) as an oil.

(iv) 2-[2-(2-Dimethylaminomethyl-5-furylmethylthio)ethylamino]-5-[1-(2-dimethylaminoethyl)-2-oxopyridin-4-ylmethyl]pyrimidin-4-one 2-(2-Dimethylaminomethyl-5-furylmethylthio)ethylamine (4.00 g) and 2-nitroamino-5-[1-(2-dimethylaminoethyl)-2-oxopyridin-4-yl-methyl]pyrimidin-4-one (7.14 g) were refluxed in pyridine (50 ml) for 24 hours. The reaction mixture was evaporated under reduced pressure and the residue subjected to medium pressure column chromatography (Kieselgel 60 silica mesh - main column) using ethyl acetate:methanol (80:20→70:30) gradient elution. The fractions containing the desired title product were evaporated in vacuo and treated with maleic acid (1.79 g) in isopropanol. The solvent was evaporated under reduced pressure and the residue washed with acetone and cold isopropanol. On standing at 5° C. the residue crystallised from ethanol-methanol to yield 2-[2-(2-dimethylaminomethyl-5-furylmethylthio)ethylamino]-5-[1-(2-dimethylaminoethyl)-2-oxopyridin-4-ylmethyl]pyrimidin-4-one as a maleate salt (0.79 g), m.p. 123°–126° C.

EXAMPLE 9

2-[3-[3-Piperidinomethyl)phenoxy]propylamino]-5-(1-n-butyl-2-oxopyridin-4-ylmethyl)pyrimidin-4-one 3-[3-Piperidinomethyl)phenoxy]propylamine (1.37 g) and 2-nitroamino-5-(1-n-butyl-2-oxopyridin-4-ylmethyl)pyrimidin- 4-one (1.60 g) were refluxed in ethanol (12 ml) for 72 hours. As starting-material was still present the ethanol was replaced by pyridine (12 ml) and the solution refluxed for a further 24 hours. The reaction mixture was evaporated under reduced pressure and the residue was washed with diethyl ether. The residue which comprised the title compound was treated with isopropanol containing ethanolic HCl and was evaporated under reduced pressure. The resultant material was recrystallised from isopropanol to afford 2-[3-[3-piperidinomethyl)phenoxy]propylamino]-5-(1-n-butyl-2-oxopyridin-4-ylmethyl)pyrimidin-4-one dihydrochloride (1.81 g), m.p. 178.5°–179.5° C.

EXAMPLE 10

2-[3-[3-(Piperidinomethyl)phenoxy]propylamino]-5-(1-methyl-2-oxopyridin-4-ylmethyl)pyrimidin-4-one 3-[3-(Piperidinomethyl)phenoxy]propylamine (1.12 g) and 2-nitroamino-5-(1-methyl-2-oxopyridin-4-ylmethyl)pyrimidin-4-one (1.11 g) were refluxed in ethanol (8 ml) for 20 hours. As the reaction was incomplete the ethanol was replaced by pyridine (8 ml) and the solution refluxed for a further 6 hours. The reaction mixture was evaporated under reduced pressure and the residue was subjected to medium pressure chromatography on silica gel (eluting with 10% methanol/90% chloroform) to afford the title compound. This was treated with dilute ethanolic HCl to afford material which was recrystallised from isopropanol/ether to afford 2-[3-[3-(piperidinomethyl)phenoxy]propylamino]-5-(1-methyl-2-oxopyridin-4-ylmethyl)pyrimidin-4-one dihydrochloride (0.85 g), m.p. 164°–167° C.

EXAMPLE 11

2-[3-[4-(Piperidinomethyl)pyrid-2-yloxy]propylamino]-5-(1-methyl-2-oxopyridin-4-ylmethyl)pyrimidin-4-one 3-[4-(Piperidinomethyl)pyrid-2-yloxy]propylamine (1.12 g) and 2-nitroamino-5-(1-methyl-2-oxopyridin-4-ylmethyl)pyrimidin-4-one (1.11 g) were refluxed in ethanol (20 ml) for 40 hours. The reaction mixture was evaporated under reduced pressure and the residue was subjected to medium pressure chromatography on silica gel (eluting with 5% methanol/95% chloroform) to afford the title compound. This was dissolved in isopropanol and treated with a solution of maleic acid (0.51 g) in isopropanol to afford material which was recrystallised from isopropanol/methanol to afford 2-[3-[4-(piperidinomethyl)pyrid-2-yloxy]propylamino]-5-(1-methyl-2-oxopyridin-4-ylmethyl)pyrimidin-4-one dimaleate (0.51 g), m.p. 115°–116.5° C.

EXAMPLE 12

2-[2-[4-(Dimethylaminomethyl)pyrid-2-ylmethylthio]ethylamino]-5-(1-methyl-2-oxopyridin-4-ylmethyl)-pyrimidin-4-one 2-[4-(Dimethylaminomethyl)pyrid-2-ylmethylthio]ethylamine (0.63 g) and 2-nitroamino-5-(1-methyl-2-oxopyridin-4-ylmethyl)pyrimidin-4-one (0.69 g) were refluxed in ethanol (12 ml) for 72 hours. As the reaction was not complete, the ethanol was replaced by pyridine (12 ml) and the solution refluxed for a further 6 hours. The reaction mixture was evaporated under reduced pressure to afford a residue which was washed with diethyl ether and recrystallised from isopropanol/ether to give 2-[2-[4-(dimethylaminomethyl)pyrid-2-ylmethylthio]ethylamino]-5-(1-methyl-2-oxopyridin-4-ylmethyl)pyrimidin-4-one (0.62 g), m.p. 137°–139° C.

EXAMPLE 13

2-[2-[4-(Dimethylaminomethyl)pyrid-2-ylmethylthio]ethylamino]-5-(1-n-butyl-2-oxopyridin-4-ylmethyl)-pyrimidin-4-one 2-[4-(Dimethylaminomethyl)pyrid-2-ylmethylthio]ethylamine (0.90 g) and 2-nitroamino-5-(1-n-butyl-2-oxopyridin-4-ylmethyl)pyrimidin-4-one (1.12 g) were refluxed in ethanol (15 ml) for 72 hours. As the reaction had not gone to completion, the ethanol was replaced by pyridine (15 ml) and the mixture was refluxed for a further 6 hours.

The reaction mixture was evaporated under reduced pressure to give the title compound as a residue. This was washed with diethyl ether, dissolved in isopropanol and treated with ethanolic HCl (5 ml). The solvent was evaporated under reduced pressure and the residue recrystallised from isopropanol/methanol to give 2-[2-[4-(dimethylaminomethyl)pyrid-2-ylmethylthio]ethylamino]-5-(1-n-butyl-2-oxopyridin-4-ylmethyl)pyrimidin-4-one trihydrochloride (1.48 g), m.p. 143°–146° C.

EXAMPLE 14

A pharmaceutical composition for oral administration is prepared by mixing together the product of Example 2 (55% wt/wt), dibasic calcium phosphate dihydrate (20%) and colouring agent (0.5%), adding a concentrated solution of polyvinylpyrrolidine (4%), granulating, drying and screening the dried granules; adding microcrystalline cellulose (8%), maize starch (8%), sodium glycollate (4%) and magnesium stearate (0.5%) to the granules and compressing into tablets containing 100 mg, 150 mg or 200 mg of the free base of the product of Example 2.

What is claimed is:
1. A compound of the formula (I):

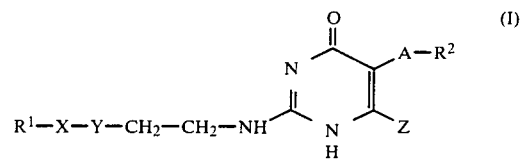

or a pharmaceutically acceptable salt thereof, wherein $R^1$ is 2- or 4- imidazolyl optionally substituted by one $C_{1-6}$alkyl, halo, trifluoromethyl or hydroxymethyl;
1-thiazolyl;
2-guanidino-4-thiazolyl optionally substituted by one chloro, bromo or $C_{1-6}$alkyl;
2-(5-amino-1,3,4-thiadiazolyl);
3-isothiazolyl optionally substituted by one chloro or bromo;
3-(1,2,5)-thiadiazolyl optionally substituted by one chloro or bromo;
2-pyridyl optionally substituted by one $C_{1-6}$alkyl, $C_{1-6}$alkoxy, halo, amino or hydroxy moiety or substituted in the 4-position by a group $R^3R^4N(CH_2)_m$—wherein $R^3$ and $R^4$ are independently hydrogen, $C_{1-6}$alkyl, aryl($C_{1-6}$)alkyl, thienyl($C_{1-6}$)alkyl, furyl($C_{1-6}$)alkyl, hydroxy($C_{1-6}$)alkyl, halo($C_{1-6}$)alkyl or $C_{3-8}$cycloalkyl; or together with the nitrogen atom to which they are attached form a 5–8 membered saturated ring; and m is 1 to 6;
2-furyl or 2-thienyl either optionally substituted in the 5-position by $R^5R^6N(CH_2)_m$—wherein $R^5$ and $R^6$ are independently hydrogen, $C_{1-6}$alkyl, $C_{3-8}$cycloalkyl, halo($C_{1-6}$)alkyl, $C_{3-6}$alkenyl, aryl ($C_{1-6}$)alkyl, $C_{3-6}$alkynyl, hydroxy($C_{1-6}$)alkyl, $C_{1-3}$alkoxy($C_{1-6}$)alkyl, trifluoro($C_{1-6}$)alkyl, amino($C_{1-6}$)alkyl, $C_{1-3}$alkylamino($C_{1-6}$)alkyl or di-($C_{1-3}$)alkylamino($C_{1-6}$)alkyl; or $R^5$ and $R^6$ together with the nitrogen atom to which they are attached form a 5–8 membered saturated ring; phenyl optionally substituted by one $C_{1-6}$alkyl, $C_{1-6}$alkoxy, hydroxy, halo, trifluoromethyl, nitro, amino, $C_{1-6}$alkylamino, $C_{1-6}$alkanoylamino, di-($C_{1-6}$)alkylamino or cyano and further optionally substituted in any of the 3-, 4-, or 5-positions on the phenyl ring by —$(CH_2)_mNR^5R^6$, —$OCH_2CH_2NR^5R^6$ or —$OCH_2CH_2CH_2NR^5R^6$;
X is methylene, or if $R^1$ is optionally substituted pyridyl or phenyl, X may also be oxygen;
Y is sulfur or methylene, provided that at least one of X and Y is methylene;
Z is hydrogen or $C_{1-6}$alkyl;
A is $C_{1-5}$methylene or —$(CH_2)_pW(CH_2)_q$ where W is oxygen or sulphur and p and q are such that their sum is from 1 to 4;
$R^2$ is a pyridone moiety substituted on the nitrogen atom by a group $R^7$ wherein $R^7$ is —$(CH_2)_rNR^8R^9$ wherein $R^8$ and $R^9$ are independently hydrogen, $C_{1-6}$alkyl, $C_{3-8}$cycloalkyl, $C_{3-6}$alkenyl, aryl($C_{1-6}$)alkyl, $C_{3-6}$alkynyl, hydroxy($C_{1-6}$)alkyl, $C_{1-3}$alkoxy($C_{1-6}$)alkyl, trifluoro($C_{1-6}$)alkyl, amino($C_{1-6}$)alkyl, $C_{1-3}$alkylamino($C_{1-6}$)alkyl or di-($C_{1-3}$)alkylamino($C_{1-6}$)alkyl; or $R^8$ and $R^9$ together with the nitrogen atom to which they are attached form a pyrrolidino, piperidino or hexahydroazepino ring, and r is 2 to 6; or $R^7$ is $C_{1-6}$alkyl, $C_{3-7}$cycloalkyl$C_{1-6}$alkyl, hydroxy$C_{2-6}$alkyl, $C_{1-6}$alkoxy$C_{2-6}$alkyl, aryl($C_{1-6}$)alkoxy$C_{2-6}$alkyl, aryloxy$C_{2-6}$alkyl or aryl($C_{1-6}$)alkyl; and the pyridone moiety is optionally substituted on a carbon atom by one $C_{1-4}$alkyl, $C_{1-4}$alkoxy, hydroxy, halo, amino or phenoxy.

2. A compound according to claim 1 wherein X is methylene when $R^1$ is optionally substituted 2-pyridyl.

3. A compound according to either claim 1 or 2 wherein $R^1$ is of the sub-formula (i)

$$R^{14}R^{15}NCH_2-R^{16}-X-Y-CH_2CH_2NH- \qquad (i)$$

wherein $R^{14}$ and $R^{15}$ are independently $C_{1-6}$alkyl or together with the nitrogen atom to which they are attached form a pyrrolidino or piperidino ring; and $R^{16}$ is 4-pyrid-2-yl, 5-furan-2-yl or 1,3-phenylene.

4. A compound according to claim 3 wherein $R^{16}$ is 5-furan-2-yl or 1,3-phenylene.

5. A compound according to claim 1 wherein $R^1-X-Y-$ is:
3-dimethylaminomethylphenoxymethyl,
3-piperidinomethylphenoxymethyl,
5-dimethylaminomethylfuran-2-ylmethylthio,
4-dimethylaminomethylpyrid-2-ylmethylthio,
4-piperidinomethylpyrid-2-ylmethylthio,
4-dimethylaminomethylpyrid-2-yloxymethyl, or
4-piperidinomethylpyrid-2-yloxymethyl.

6. A compound according to claim 1 wherein A is methylene.

7. A compound according to claim 1 wherein Z is hydrogen.

8. A compound according to claim 1 wherein $R^2$ is in the form:

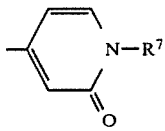

9. A compound according to claim 1 wherein $R^7$ is methyl, ethyl, n-butyl, benzyl or dimethylaminoethyl.

10. A compound according to claim 1 which is: 2-[2-(5-methyl-4-imidazolylmethylthio)ethylamino]-5-(1-methyl-2-oxopydridin-4-ylmethyl)pyrimidin-4-one or a pharmaceutically acceptable salt thereof.

11. A compound according to claim 1 which is: 2-[2-(2-dimethylaminomethyl-5-furylmethylthio)ethylamino]-5-(1-methyl-2-oxopyridin-4-ylmethyl)pyrimidin-4-one or a pharmaceutically acceptable salt thereof.

12. A compound according to claim 1 which is: 2-[2-(5-methyl-4-imidazolylmethylthio)ethylamino]-5-(1-n-butyl-2-oxopyridin-4-ylmethyl)pyrimidin-4-one or a pharmaceutically acceptable salt thereof.

13. A compound according to claim 1 which is: 2-[2-(2-dimethylaminomethyl-5-furylmethylthio)ethylamino]-5-(1-n-butyl-2-oxopyridin-4-ylmethyl)pyrimidin-4-one or a pharmaceutically acceptable salt thereof.

14. A compound according to claim 1 which is: 2-[2-(2-guanidino-4-thiazolylmethylthio)ethylamino]-5-(1-n-butyl-2-oxopyridin-4-ylmethyl)pyrimidin-4-one or a pharmaceutically acceptable salt thereof.

15. A compound according to claim 1 which is: 2-[2-(5-methyl-4-imidazolylmethylthio)ethylamino]-5-(1-benzyl-2-oxopyridin-4-ylmethyl)pyrimidin-4-one or a pharmaceutically acceptable salt thereof.

16. A compound according to claim 1 which is: 2-[2-(2-dimethylaminomethyl-5-furylmethylthio)ethylamino]-5-(1-benzyl-2-oxopyridin-4-ylmethyl)pyrimidin-4-one or a pharmaceutically acceptable salt thereof.

17. A compound according to claim 1 which is: 2-[2-(2-dimethylaminomethyl-5-furylmethylthio)ethylamino]-5-[1-(2-dimethylaminoethyl)-2-oxopyridin-4-ylmethyl]pyrimidin-4-one or a pharmaceutically acceptable salt thereof.

18. A compound according to claim 1 which is: 2-[3-[3-piperidinomethyl)phenoxy]propylamino]-5-(1-n-butyl-2-oxopyridin-4-ylmethyl)pyrimidin-4-one or a pharmaceutically acceptable salt thereof.

19. A compound according to claim 1 which is: 2-[3-[3-piperidinomethyl)phenoxy]propylamino]-5-(1-methyl-2-oxopyridin-4-ylmethyl)pyrimidin-4-one or a pharmaceutically acceptable salt thereof.

20. A compound according to claim 1 which is: 2-[3-[4-piperidinomethyl)pyrid-2-yloxy]propylamino]-5-(1-methyl-2-oxopyridin-4-ylmethyl)pyrimidin-4-one or a pharmaceutically acceptable salt thereof.

21. A compound according to claim 1 which is: 2-[2-[4-dimethylaminomethyl)pyrid-2-ylmethylthio]ethylamino]-5-(1-methyl-2-oxopyridin-4-ylmethyl)pyrimidin-4-one or a pharmaceutically acceptable salt thereof.

22. A compound according to claim 1 which is: 2-[2-[4-dimethylaminomethyl)pyrid-2-ylmethylthio]ethylamino]-5-(1-n-butyl-2-oxopyridin-4-ylmethyl)pyrimidin-4-one or a pharmaceutically acceptable salt thereof.

23. A compound according to claim 1 which is: 2-[2-(dimethylaminomethyl-5-furan-2-ylmethylthio)ethylamino]-5-(1-methyl-2-oxopyridin-4-ylmethyl)pyrimidin-4-one trihydrochloride.

24. A compound according to claim 1 which is: 2-[3-[4-piperidinomethyl)pyrid-2-yloxy]propylamino]-5-(1-methyl-2-oxopyridin-4-ylmethyl)pyrimidin-4-one.

25. A pharmaceutical composition having histamine $H_2$-antagonist activity which comprises a compound according to claim 1 and a pharmaceutically acceptable carrier.

26. A method of blocking histamine $H_2$-receptors which comprises administering to an animal an effective amount to block said receptors of a compound of claim 1.

27. A compound of the formula (III):

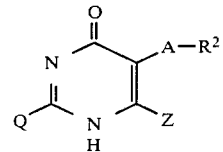

wherein

Z is hydrogen or $C_{1-6}$alkyl;

A is $C_{1-5}$methylene or $-(CH_2)_pW(CH_2)_q$ where W is Oxygen or sulphur and p and q are such that their sum is from 1 to 4;

$r^2$ is a pyridone moiety substituted on the nitrogen atom by a group $R^7$ wherein $R^7$ is $-(CH_2)_rNR^8R^9$ wherein $R^8$ and $R^9$ are independently hydrogen, $C_{1-6}$alkyl, $C_{3-8}$cycloalkyl, $C_{3-6}$alkenyl, aryl($C_{1-6}$)alkyl, $C_{3-6}$alkynyl, hydroxy($C_{1-6}$)alkyl, $C_{1-3}$alkoxy($C_{1-6}$)alkyl, trifluoro($C_{1-6}$)alkyl, amino($C_{1-6}$)alkyl, $C_{1-3}$alkylamino($C_{1-6}$)alkyl or di-($C_{1-3}$)alkylamino($C_{1-6}$)alkyl; or $R^8$ and $R^9$ together with the nitrogen atom to which they are attached form a pyrrolidino, piperidino or hexahydroazepino ring, and r is 2 to 6; or $R^7$ is $C_{1-6}$alkyl, $C_{3-7}$cycloalkyl$C_{1-6}$alkyl, hydroxy$C_{2-6}$alkyl, $C_{1-6}$alkoxy$C_{2-6}$alkyl, aryl($C_{1-6}$)alkoxy$C_{2-6}$alkyl, aryloxy$C_{2-6}$alkyl or aryl($C_{1-6}$)alkyl; and the pyridone moiety is optionally substituted on a carbon atom by one $C_{1-4}$alkyl, $C_{1-4}$alkoxy, hydroxy, halo, amino or phenoxy; and Q is a group displaceable by amine.

* * * * *

UNITED STATES PATENT AND TRADEMARK OFFICE
CERTIFICATE OF CORRECTION

PATENT NO. : 4,540,699
DATED : September 10, 1985
INVENTOR(S) : Thomas H. Brown and Derek A. Rawlings It is certified that error appears in the above-identified patent and that said Letters Patent is hereby corrected as shown below:

Column 1, lines 20-22, should read
-- which block these histamine $H_2$-receptors are called histamine $H_2$-antagonists.
   Histamine $H_2$-antagonists are useful in treating disease --.

Column 11, line 2, "is replaced by provided that is" should read -- is replaced by $R^{18}$; provided that $R^{18}$ is --.

Column 24, line 61, "$r^2$" should read -- $R^2$ --.

Signed and Sealed this

Seventeenth Day of December 1985

[SEAL]

Attest:

DONALD J. QUIGG

Attesting Officer

Commissioner of Patents and Trademarks